United States Patent
Howie et al.

(10) Patent No.: US 7,824,409 B2
(45) Date of Patent: Nov. 2, 2010

(54) MODULAR IMPACTION GRAFTING TAMPS

(75) Inventors: Donald W. Howie, Tennyson (AU); Douglas E. Padgett, New York, NY (US); Stephen H. Hoag, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 593 days.

(21) Appl. No.: 10/356,029

(22) Filed: Jan. 31, 2003

(65) Prior Publication Data
US 2004/0153082 A1 Aug. 5, 2004

(51) Int. Cl.
*A61B 17/56* (2006.01)

(52) U.S. Cl. .................................... 606/86 R

(58) Field of Classification Search ............... 606/86, 606/95, 99, 105, 86 R; 623/20.35, 20.36, 623/22.41, 22.42, 22.45, 22.46, 23.18, 23.44
See application file for complete search history.

(56) References Cited

U.S. PATENT DOCUMENTS

| | | | | |
|---|---|---|---|---|
| 4,706,659 | A | * 11/1987 | Matthews et al. | 606/80 |
| 5,074,879 | A | * 12/1991 | Pappas et al. | 623/23.46 |
| 5,078,746 | A | 1/1992 | Garner | |
| 5,080,685 | A | * 1/1992 | Bolesky et al. | 623/22.42 |
| 5,470,336 | A | * 11/1995 | Ling et al. | 606/105 |
| 5,507,830 | A | * 4/1996 | DeMane et al. | 623/22.42 |
| 5,782,921 | A | * 7/1998 | Colleran et al. | 623/20.15 |
| 5,925,051 | A | * 7/1999 | Mikhail | 606/94 |
| 6,013,080 | A | * 1/2000 | Khalili | 606/86 R |
| 6,902,583 | B2 | * 6/2005 | Gerbec et al. | 623/23.47 |
| 2002/0040244 | A1 | * 4/2002 | Despres et al. | 623/22.15 |
| 2003/0204269 | A1 | * 10/2003 | Gerbec et al. | 623/23.47 |

OTHER PUBLICATIONS

"Impaction Grafting System," Biomet, http://www.biomet.com/hips/rev_impactgraft.cfm, Dec. 16, 2002 (2 pages).
"Impaction Grafting for Revision Total Hip Arthroplasty," University of Pennsylvania Orthopaedic Journal, http://www.uphs.upenn.edu/ortho/oj/1997/oj10sp97pl.html, Dec. 16, 2002 (7 pages).
"Joint replacement," Gale Encyclopedia of Medicine, http://www.findarticles.com/cf_dls/g2601/0007/2601000783/print.jhtml, May 2, 2003 (4 pages).

* cited by examiner

*Primary Examiner*—Eduardo C Robert
*Assistant Examiner*—David Comstock
(74) *Attorney, Agent, or Firm*—Baker & Daniels LLP (57) ABSTRACT

Methods for impaction grafting an intramedullary canal of a bone including a first canal portion and a second canal portion spaced along a canal axis. A first tamp may be moved axially within the canal to impaction graft the first canal portion. A second tamp may be mounted to the first tamp in axial sliding relationship and moved axially within the canal relative to the first tamp to impaction graft the second canal portion. The first and second tamps may be locked together in fixed axial relationship to prevent relative axial movement between the first tamp and the second tamp while the first tamp is moved to impaction graft the first canal portion before impaction grafting the first canal portion. The first and second tamps may be unlocked to permit relative axial sliding of the first and second tamps before impaction grafting the second canal portion.

11 Claims, 7 Drawing Sheets

MODULAR IMPACTION GRAFTING TAMPS

FIELD OF THE INVENTION

The present invention relates generally to the field of orthopaedics, and, more particularly, to impaction grafting tamps.

BACKGROUND[1]

Arthroplasty is surgery to relieve pain and restore range of motion by realigning or reconstructing a joint. Typical arthroplastic options include joint resection, interpositional reconstruction, and total joint replacement. Joint resection involves removing a portion of a bone from a joint to create a gap between the bone and the corresponding socket, thereby improving the range of motion. Scar tissue eventually fills the gap. Pain may be relieved and motion restored, but the joint is typically less stable. Interpositional reconstruction reshapes the joint and adds a prosthetic disk between the bones forming the joint. The prosthesis can be made of plastic and metal or from body tissue such as fascia and skin. If the joint does not respond to the more conservative treatments (which may include medication, weight loss, activity restriction, and/or use of walking aids such as a cane), joint replacement is often considered appropriate. Joint replacement (i.e., total joint arthroplasty) is the surgical replacement of a joint with a prosthesis. Many joint replacements are needed because arthritis has caused the joint to stiffen and become painful to the point where normal daily activities are no longer possible. Arthroplasty, especially joint replacement, is becoming an increasingly prevalent treatment. For example, it has been reported that more than 170,000 hip replacements and more than 200,000 knee replacements are performed in the United States each year.

[1] See Gale Encyclopedia of Medicine, Gale Research (1999), found at http://www.findarticles.com/cf_dls/g2601/0007/2601/000783/p1/article.jhtml-?term=.

A conventional hip prosthesis includes an artificial socket and a femoral stem. The artificial socket is typically made of metal coated and polyethylene (a plastic) to reduce friction. The femoral stem has a ball at one end and an elongated post or spike at the other. In a relatively simple hip replacement operation, the surgeon makes an incision in the area of the distal femur and then pulls the distal femur away from the acetabulum (socket of the hip bone). Next, the surgeon inserts the artificial socket into the acetabulum. The surgeon cuts and shapes the distal femur, inserts the post of the femoral stem into the medullary canal of the distal femur, and fits the ball of the stem into the artificial socket. The surgeon secures the artificial socket and the post of the stem within the acetabulum and the medullary canal, respectively, with an acrylic polymer (a synthetic cement). Alternatively, the artificial socket and the post may be designed for fixation by natural bone in-growth.

However, not all hip replacements are so simple. Impaction grafting is increasingly incorporated in cases that are complicated by substantial bone loss within the femur. Impaction grafting is a technique in which the surgeon uses impaction grafting tamps to impact morselized allograft (a replacement material typically made from bone chips, among other things) into the medullary canal of the femur. The allograft creates a new canal for receiving the femoral stem.

Conventional impaction grafting approaches include progressively impacting the subject bone cavity with allograft to ensure a high overall finished graft integrity. But properly aligning and otherwise manipulating the differently sized and shaped tamps needed for progressive impaction grafting has been challenging.

SUMMARY OF THE INVENTION

The present invention provides an apparatus including a plurality of separable impaction grafting tamps coupled to form an integrated impaction grafting tamp.

In an alternative embodiment, the present invention provides an apparatus including a first impaction grafting tamp defining a first channel including a sleeve portion. The apparatus further includes an elongated member including an elongated first portion and an elongated second portion together defining a second channel. The first portion of the elongated member is positioned in the sleeve portion of the first channel, and the first channel communicates with the second channel to form an integrated channel including a first opening and a second opening axially spaced apart from the first opening.

In another alternative embodiment, the present invention provides an apparatus for impaction grafting a canal including a first portion and a second portion. The apparatus includes a first means for impaction grafting the first portion of the canal, and further includes a second means, removably coupled to the first means, for impaction grafting the second portion of the canal.

The above-noted features and advantages of the present invention, as well as additional features and advantages, will be readily apparent to those skilled in the art upon reference to the following detailed description and the accompanying drawings.

DETAILED DESCRIPTION OF EXEMPLARY EMBODIMENT(S)

Although various views of the drawings may be identified herein as "anterior plan," "medial plan," "lateral plan," and the like, it is noted that these view designations are merely for clarity of exposition and, accordingly, they do not indicate limitations of the present invention.

Figure 1:
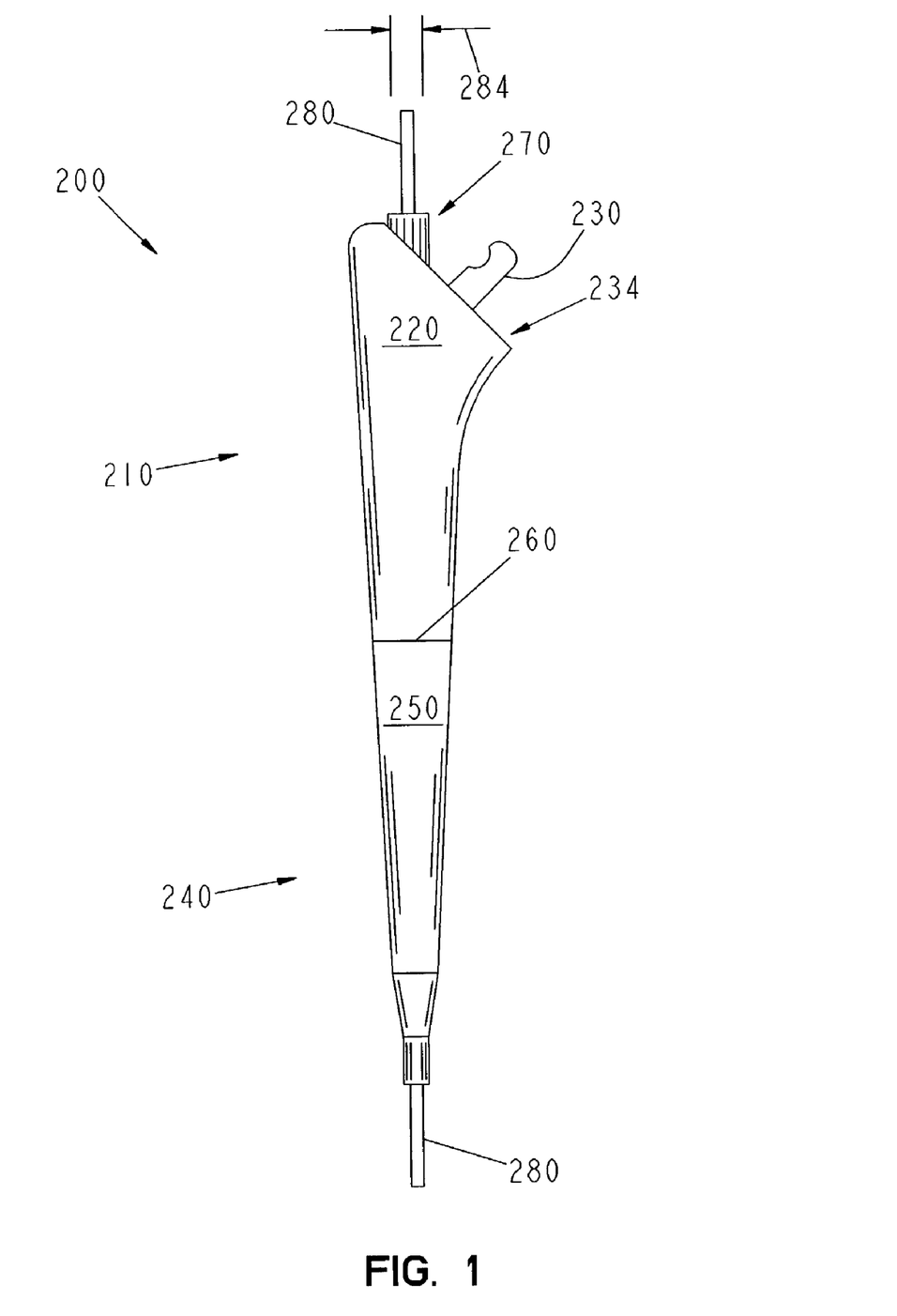
FIG. 1 shows an anterior plan view of an exemplary apparatus according to the present invention.

FIG. 1 shows an anterior plan view of an exemplary apparatus 200 according to the present invention. The various components of exemplary apparatus 200 described herein are made from stainless steel, plastic, or any other material suitable for use in surgical procedures, and they are of suitable size and weight for manipulation by hand. Additionally, the components of exemplary apparatus 200 are reusable, and accordingly, are made suitable for sterilization in an autoclave. Referring to FIG. 1, exemplary apparatus 200 includes an impaction grafting tamp 210. Tamp 210 includes an outer, tamping surface 220 and further includes a notched post 230. Next to post 230, tamp 210 also includes an inwardly extending generally cylindrical bore 234 (see FIG. 2, FIG. 4, and FIG. 5). In general, surface 220 is tapered and otherwise suitably shaped for tamping allograft into a proximal portion of a distal femur.

Apparatus 200 further includes an impaction grafting tamp 240. Tamp 240 includes an outer, tamping surface 250 that is narrowly spaced apart from surface 220 by a small (approximately 0.010 inches wide) gap 260. In general, surface 250 is tapered and otherwise suitably shaped for tamping allograft into a distal portion of the distal femur. Gap 260 is large enough to prevent the edges of surface 220 and surface 250 from wearing on each other, yet gap 260 is small enough to prevent allograft from becoming trapped between the tamp 210 and tamp 240 during operation. It should be appreciated, then, that surface 220 and surface 250 together form a generally tapered, practically continuous tamping surface. In alternative embodiments, surface 220 and/or surface 250 may include any suitable additional tapering or even overlapping at gap 260 to otherwise inhibit entrapment of allograft between tamp 210 and tamp 240. It is reiterated, however, that apparatus 200 is merely exemplary. In alternative embodiments tamp 210 and/or tamp 240 may be replaced by one or more other suitably sized and shaped impaction grafting tamps for impaction grafting a distal femur or any other bone cavity.

Further, apparatus 200 includes a connecting screw 270 and a cylindrical smooth guide rod 280. Rod 280 has a diameter or width 284. As discussed in further detail below, screw 270 holds tamp 210 together with tamp 240, and rod 280 extends through screw 270 and tamp 240.

Figure 2:
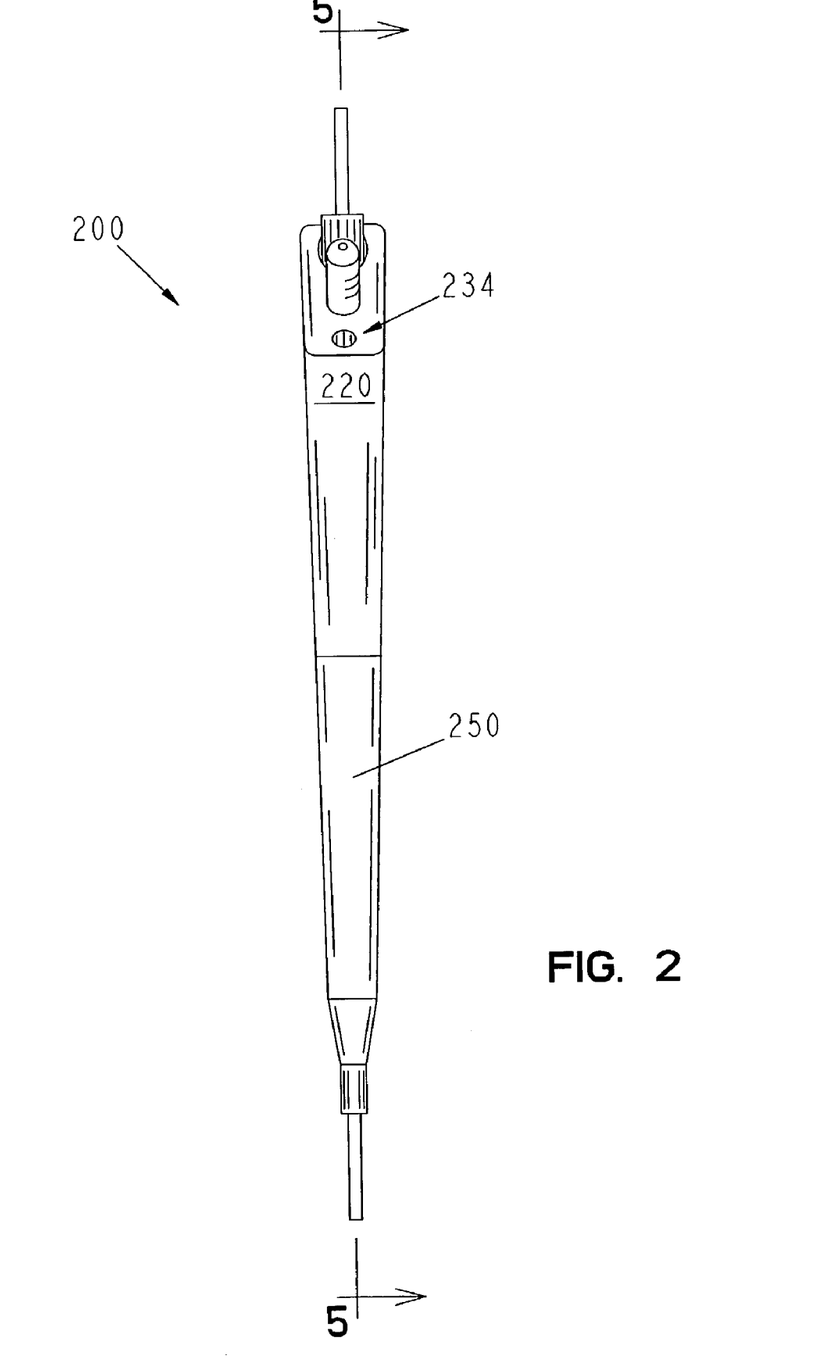
FIG. 2 shows a medial plan view of the exemplary apparatus.
Figure 3:
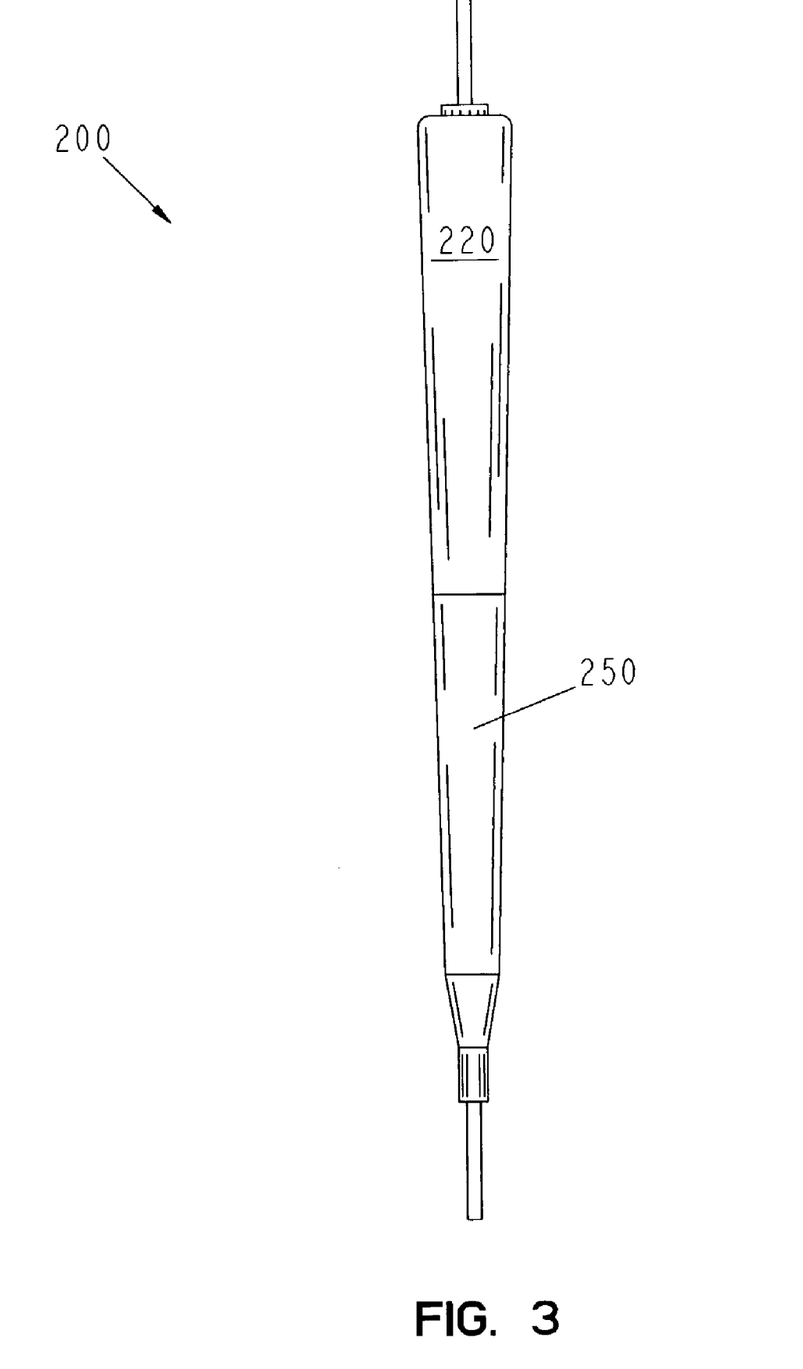
FIG. 3 shows a lateral plan view of the exemplary apparatus.

FIG. 2 shows a medial plan view of exemplary apparatus 200. Bore 234 and additional portions of surface 220 and surface 250, among other things, are discernable in FIG. 2. Meanwhile, FIG. 3 shows a lateral plan view of exemplary apparatus 200. Yet additional portions of surface 220 and surface 250, among other things, are discernable in FIG. 3.

Figure 4:
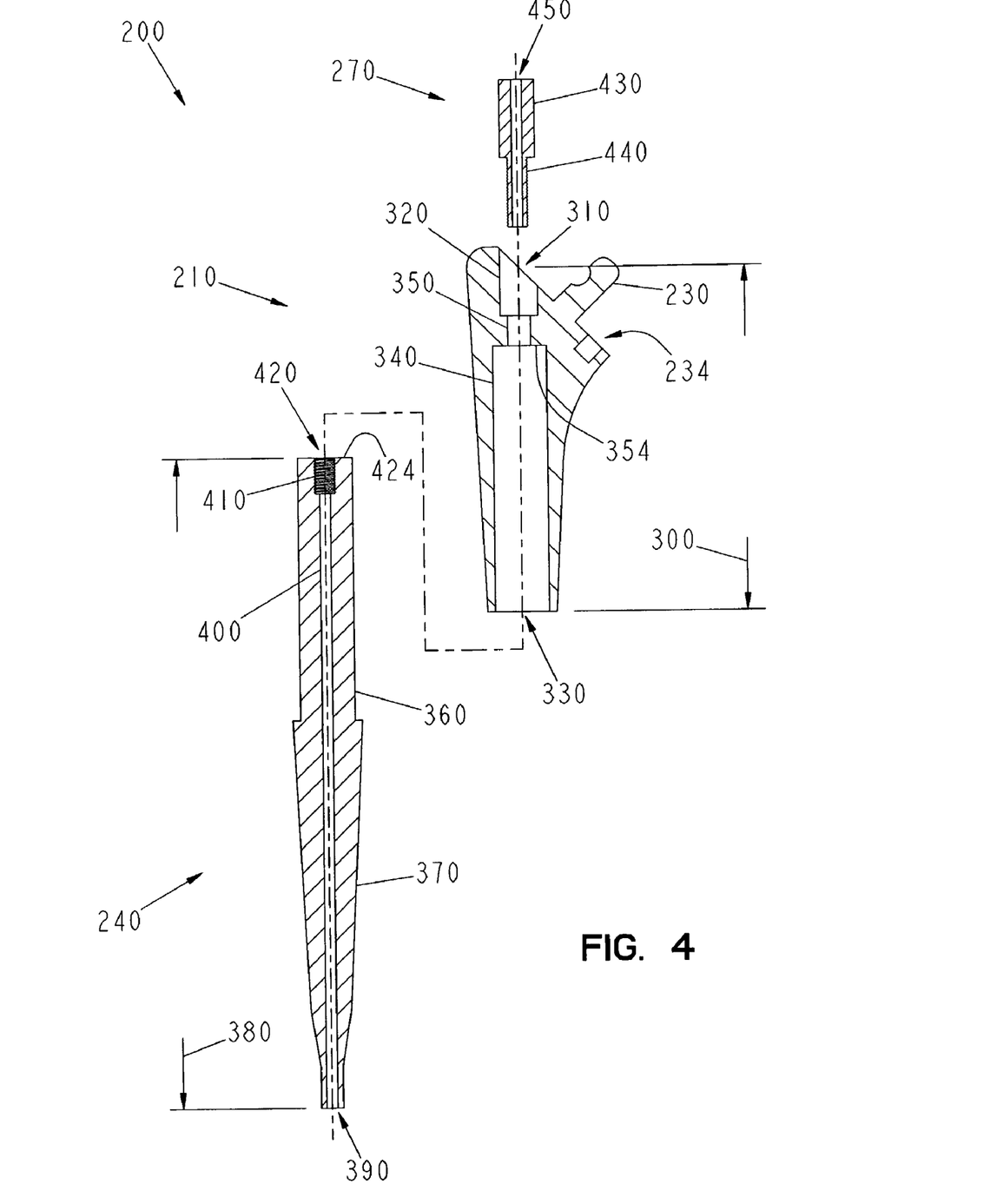
FIG. 4 shows an exploded cross-sectional view of the exemplary apparatus (without the guide rod), along line 5-5 of FIG. 2.

FIG. 4 shows an exploded cross-sectional view of exemplary apparatus 200 (without guide rod 280), along line 5-5 of FIG. 2. As discernable in FIG. 4, tamp 210 defines an elongated channel 300. Channel 300 includes an end opening 310 and an elongated cylindrical smooth end portion 320 extending inwardly from opening 310. Further, channel 300 includes an end opening 330 and an elongated smooth portion 340 extending inwardly from opening 330. Transverse to the elongation of channel 300, portion 340 has a rectangular, elliptical, or any otherwise noncircular cross-sectional shape. In alternative embodiments, portion 340 may be cylindrical. Additionally, channel 300 includes a cylindrical smooth intermediate portion 350 extending between portion 320 and portion 340. The diameter or width of portion 320 (transverse to the elongation of channel 300) is greater than the diameter or width (transverse to the elongation of channel 300) of portion 350; the width of portion 340 (transverse to the elongation of channel 300) is greater than the diameter or width (transverse to the elongation of channel 300) of portion 320; and the width of portion 340 (transverse to the elongation of channel 300) is greater than the diameter or width (transverse to the elongation of channel 300) of portion 350. Channel 300 also includes a generally planar surface 354 rimming portion 350 and extending radially to portion 340.

Tamp 240 includes an elongated portion 360 and an elongated portion 370 that together define an elongated channel 380. Portion 360 has a transverse cross-sectional shape (transverse to the elongation of channel 380) that is about the same as, but slightly smaller than, that of portion 340 of channel 300. It should be appreciated, then, that portion 300 forms a sleeve that receives portion 360. Thus, in the exemplary embodiment portion 360 slidably (but not rotationally) engages the inside of portion 340; whereas, in alternative embodiments in which portion 340 and portion 360 are cylindrical, portion 360 slidably and rotationally engages the inside of portion 340.

Channel 380 includes an end opening 390 and an elongated smooth cylindrical portion 400 extending inwardly from opening 390. Channel 380 also includes a threaded cylindrical portion 410 and an end opening 420. Portion 410 extends between portion 400 and opening 420. The diameter or width of portion 410 (transverse to the elongation of channel 380) is slightly less than that of portion 350 of channel 300, while the diameter or width of portion 400 (transverse to the elongation of channel 380) is less than that of portion 410. Additionally, the diameter or width of portion 400 is slightly greater than diameter or width 284 of rod 280 such that rod 280 (see FIG. 1) slidably and rotationally engages the inside of portion 400. Portion 360 also includes a generally planar surface 424 rimming portion 410 and opening 420.

Screw 270 includes a cylindrical head 430 having a diameter or width about the same as that of portion 320 of channel 300. Head 430 has a textured outer surface or any other outer surface suitable for gripping and manipulating screw 270 by hand. Screw 270 further includes a threaded shaft 440 having a diameter or width slightly less than that of portion 350 of channel 300. The diameter and threading of shaft 440 corresponds to that of portion 410 of channel 380 such that shaft 440 screws into portion 410 and, thus, screw 270 holds tamp 210 together with tamp 240. Additionally, screw 270 defines a cylindrical channel 450 having a diameter or width about the same as that of portion 400 of channel 380, such that rod 280 (see FIG. 1) also slidably and rotationally engages the inside of channel 450.

Figure 5:
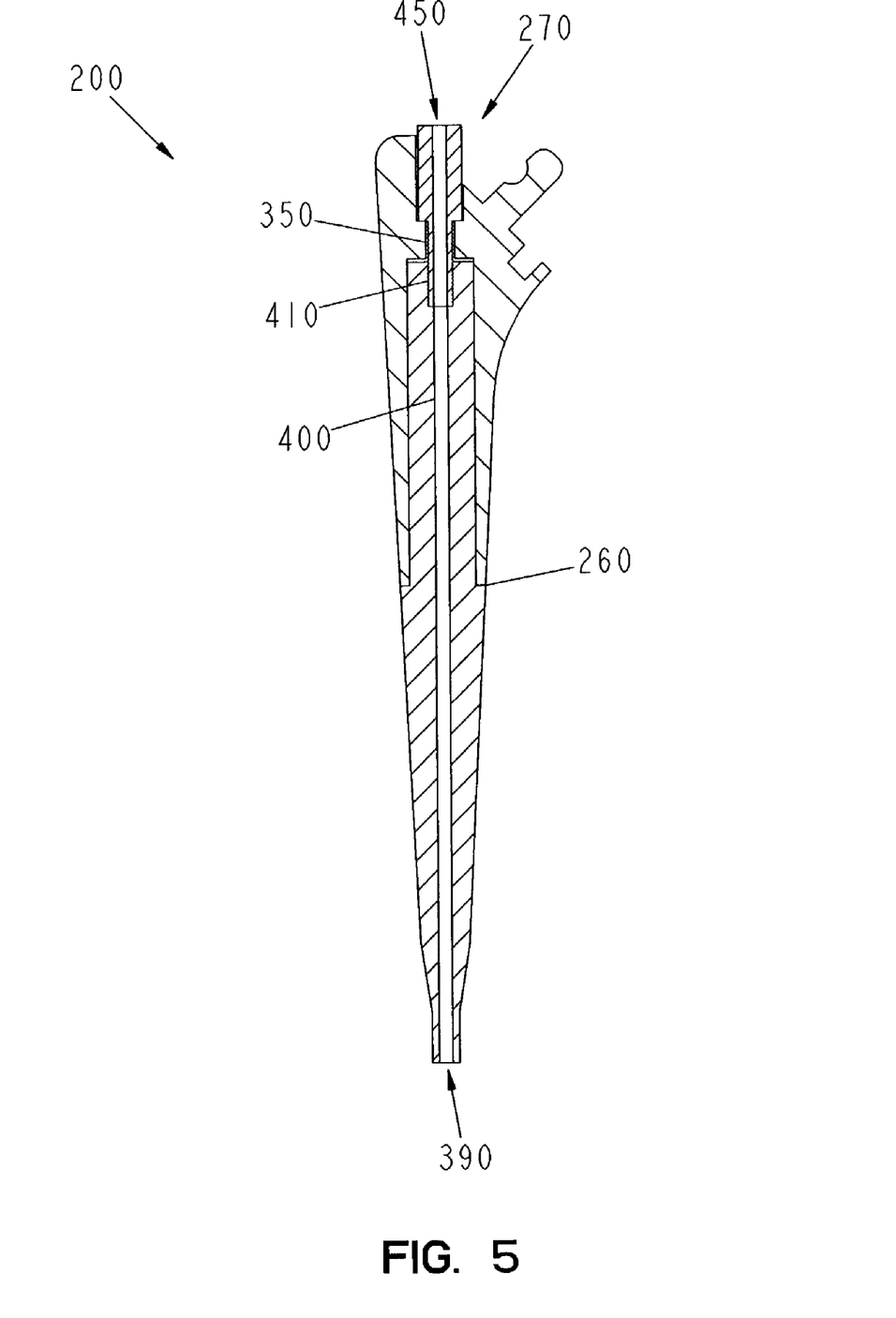
FIG. 5 shows an assembled cross-sectional view of the exemplary apparatus (without the guide rod), along line 5-5 of FIG. 2.

FIG. 5 shows an assembled cross-sectional view of exemplary apparatus 200 (without guide rod 280), along line 5-5 of FIG. 2. When fully assembled, portion 360 of tamp 240 is inserted into portion 340 of channel 300 (of tamp 210) such that surface 354 of tamp 210 meets surface 424 of tamp 240 (see FIG. 4). Further, portion 350 of channel 300 communicates with portion 410 of channel 380 (see also FIG. 4) such that channel 300 and channel 380 form an integrated channel that receives screw 270 at one end and includes opening 390 at another end. It should be appreciated that this integrated channel is defined by portion 320 of channel 300 (see FIG. 4), portion 350 of channel 300, portion 410 of channel 380, and portion 400 of channel 380. Additionally, it should be appreciated that channel 450 of screw 270 also communicates with portion 400 of channel 380 to form an integrated channel that is coaxial with the integrated channel defined by portion 320, portion 350, portion 410, and portion 400. As discussed above (see FIG. 1), tamping surface 220 remains narrowly spaced apart from tamping surface 250 by gap 260, yet the two tamps together provide a practically continuous tamping surface. Thus, it should be appreciated that when assembled tamp 210 and tamp 240 together form an aligned, integrated overall impaction grafting tamp.

FIG. 6a, FIG. 6b, FIG. 6c, and FIG. 6d show anterior plan views of guide rod 280, connecting screw 270, a connecting handle 460, and an extension member 470, respectively. In alternative embodiments, handle 460 replaces screw 270 (see, e.g., FIG. 1 and FIG. 4). Handle 460 includes a cylindrical head 480 that has a diameter or width like that of head 430 of screw 270. Further, like head 430, head 480 has a textured outer surface or any other outer surface suitable for gripping and manipulating handle 460 by hand. Handle 460 further includes a cylindrical threaded shaft 490 configured in a like manner to that of shaft 440 of screw 270. Also, handle 460 defines a cylindrical channel 500 having a diameter or width like that of channel 450 of screw 270 (see FIG. 7). However, the lengths of head 480 and channel 500 are substantially greater than the lengths of head 430 and channel 450, respectively. The longer head 480 of handle 460 provides an integral lever (or handle) for manipulating alternative embodiments of the present invention.

Figures 6A, 6B, 6C:
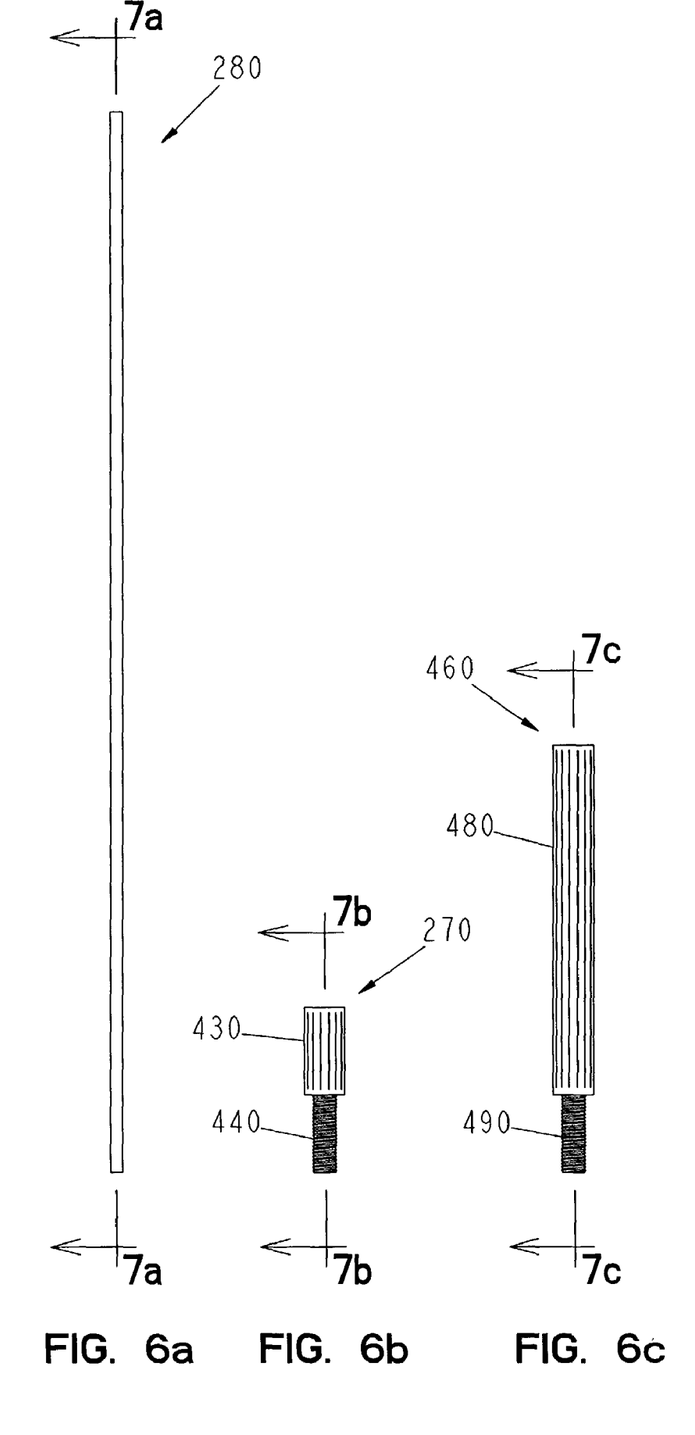
FIG. 6a, FIG. 6b, FIG. 6c, and FIG. 6d show anterior plan views of the guide rod, the connecting screw, a connecting handle, and an extension member, respectively.
Figure 6D:
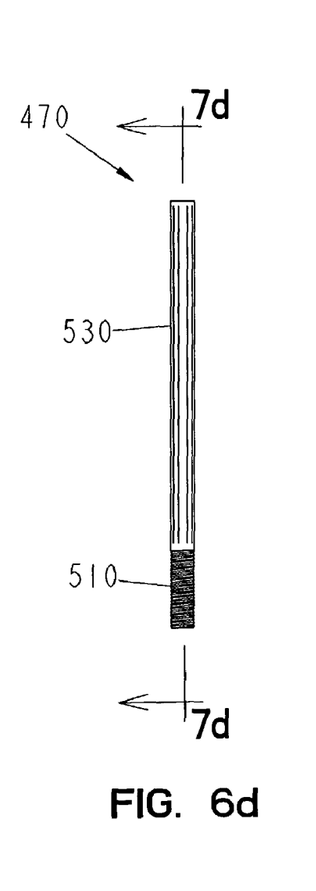
Figures 7A, 7B:
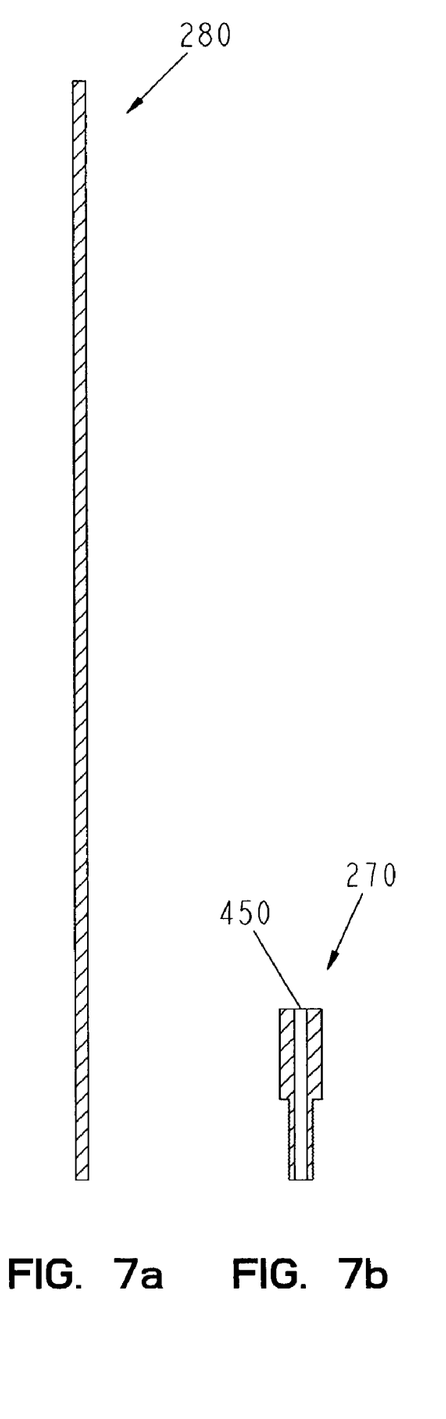
FIG. 7a, FIG. 7b, FIG. 7c, and FIG. 7d show cross-sectional views of the guide rod, connecting screw, connecting handle, and extension member, respectively, along lines 7a-7a, 7b-7b, 7c-7c, and 7d-7d of FIG. 6a, FIG. 6b, FIG. 6c, and FIG. 6d, respectively.
Figure 7C:
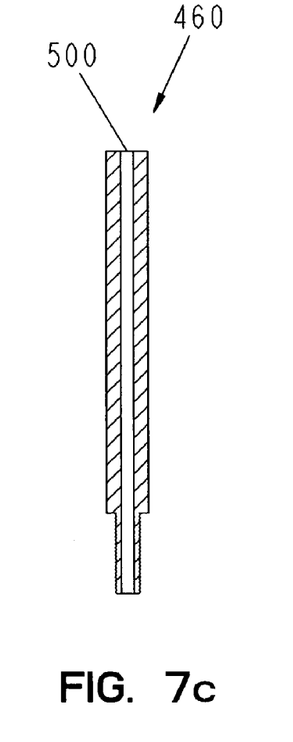
Figure 7D:
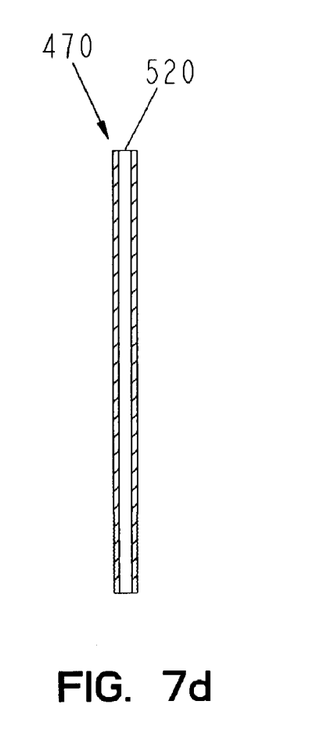

Yet other alternative embodiments include extension member 470 rather than screw 270. Member 470 includes a cylindrical threaded shaft 510 configured in a like manner to that of shaft 440 of screw 270. Also, member 470 defines a cylindrical channel 520 having a diameter or width like that of channel 450 of screw 270 (see FIG. 7). Further, member 470 includes a cylindrical head 530 of about the same length as that of head 480 of handle 460. However, head 530 is smooth, and has a diameter or width only about the same as that of shaft 510. Member 470 provides an effective extension of tamp 240 through portion 350 of channel 300 (without holding tamp 210 together with tamp 240).

FIG. 7a, FIG. 7b, FIG. 7c, and FIG. 7d show cross-sectional views of guide rod 280, connecting screw 270, connecting handle 460, and extension member 470, respectively, along lines 7a-7a, 7b-7b, 7c-7c, and 7d-7d of FIG. 6a, FIG. 6b, FIG. 6c, and FIG. 6d, respectively.

In operation of exemplary apparatus 200 for impaction grafting a distal femur, a rasp handle or any other suitable well-known handle type device is attached to tamp 210 via post 230 and/or bore 234 in a well-known manner. Next, guide rod 280 (alone) is inserted into the femoral medullary canal and suitably aligned with the longitude of the femur. Allograft is then suitably introduced into a distal part of the canal. Tamp 240 and tamp 210, while held together by screw 270 (or handle 460 in alternative embodiments), are slid over rod 280 via opening 390 (tamp 240) such that rod 280 extends through portion 400 of channel 380 (of tamp 240) and through channel 450 of screw 270 (or channel 500 of handle 460 in alternative embodiments). It should be appreciated that the engagements of tamp 240 and screw 270 (or handle 460 in alternative embodiments) with rod 280 facilitate alignment of tamp 240 and tamp 210 with the longitude of the femur. Then, tamp 240 and tamp 210, still held together by screw 270 (or handle 460 in alternative embodiments), are used to suitably tamp the allograft. The rasp handle merely facilitates manipulations of the integrated tamp as desired. After the user becomes satisfied with the resulting distal graft mantle integrity, the integrated tamp formed by tamp 240 and tamp 210 is once again inserted into the canal. Screw 270 (or handle 460 in alternative embodiments) and tamp 210 are then removed, but tamp 240 is left positioned in the distal part of the canal.

Next, with tamp 240 remaining in place, allograft is suitably introduced into the proximal part of the canal. This allograft is then suitably tamped in the proximal part of the canal by sliding portion 340 of channel 300 (of tamp 210) over portion 360 of tamp 240 and, generally, by moving surface 354 (tamp 210) to and fro surface 424 (tamp 240). It should be appreciated that the slidable engagement of tamp 210 and tamp 240 facilitates proper re-alignment of tamp 210 with the longitude of the femur. Here, the rasp handle merely facilitates manipulations of tamp 210 as desired. Additionally, it should be appreciated that in alternative embodiments portion 510 of extension rod 470 may be screwed into portion 410 of channel 380 (of tamp 240) such that head 530 of rod 470 further facilitates proper re-alignment of tamp 210.

Finally, screw 270 (or handle 460 in alternative embodiments) may be installed or re-installed through opening 310 (of tamp 210), with shaft 440 of screw 270 (or shaft 490 of handle 460 in alternative embodiments) screwed into portion 410 of channel 380 (of tamp 240). It should be appreciated that for embodiments employing member 470, member 470 must be removed prior to the installation of screw 270 or handle 460. Screw 270 (or handle 460 in alternative embodiments) again secures tamp 210 to tamp 240. This allows the integrated impaction grafting tamp to be further manipulated as desired for trial reductions (mock assemblies in which the exemplary generally stem shaped integrated tamp may be fitted into an acetabulum to test alignments and/or depths of the new canal) and/or for any other suitable work. For trial reductions with the exemplary embodiment, a suitable provisional assembly (mock or trial ball) may be attached to tamp 210 via post 230 and bore 234 in a well known manner. After the impaction grafting tamping is completed, the integrated impaction grafting tamp is removed from the canal.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A method for impaction grafting an intramedullary canal of a bone including a first canal portion and a second canal portion spaced along a canal axis, the method comprising:
   moving a first tamp axially within the canal to impaction graft the first canal portion;
   moving a second tamp, mounted to the first tamp in axial sliding relationship, axially within the canal relative to the first tamp to impaction graft the second canal portion;
   locking the first and second tamps together in fixed axial relationship to prevent relative axial movement between the first tamp and the second tamp while the first tamp is moved to impaction graft the first canal portion before impaction grafting the first canal portion; and
   unlocking the first and second tamps to permit relative axial sliding of the first and second tamps before impaction grafting the second canal portion.

2. The method of claim 1 further comprising:
   engaging an extension member with the first tamp such that the extension member projects from the first tamp; and
   engaging the second tamp with the extension member in axial sliding relationship before impaction grafting the second canal portion.

3. The method of claim 1 wherein moving the second tamp in axial sliding relationship relative to the first tamp comprises sliding an elongated female channel defined by the second tamp over an elongated male member defined by the first tamp, the female channel and male member aligning the tamps longitudinally.

4. The method of claim 1 further comprising inserting a guide rod into the intramedullary canal and wherein impaction grafting the first canal portion comprises moving the first and second tamps axially together over the guide rod and wherein impaction grafting the second canal portion comprises leaving the first tamp stationary in the first canal portion and moving the second tamp axially relative to the stationary first tamp.

5. A method for impaction grafting an intramedullary canal of a bone including a first canal portion and a second canal portion spaced along a canal axis, the method comprising:
   providing a first tamp having a first tapered portion, wherein the first tamp has a shape mimicking a femoral hip stem component;
   moving the first tamp axially within the canal to impaction graft the first canal portion;
   providing a second tamp having a second tapered portion, wherein the second tamp has a shape mimicking a femoral hip stem component, the shape of the second tamp flush with the shape of the first tamp about an interface between said tamps and cooperating to form a practically continuous tamping surface when the second tamp abuts the first tamp; and
   moving the second tamp, mounted to the first tamp in axial sliding relationship, axially within the canal relative to the first tamp from a first position in which the second tamp abuts the first tamp to impaction graft the second canal portion.

6. The method of claim 5 further comprising:
   locking the first and second tamps together in fixed axial relationship before impaction grafting the first canal portion; and
   unlocking the first and second tamps to permit relative axial sliding of the first and second tamps before impaction grafting the second canal portion.

7. The method of claim 5 further comprising:
   engaging an extension member with the first tamp such that the extension member projects from the first tamp; and
   engaging the second tamp with the extension member in axial sliding relationship before impaction grafting the second canal portion.

8. The method of claim 5 wherein moving the second tamp in axial sliding relationship relative to the first tamp comprises sliding an elongated female channel defined by the second tamp over an elongated male member defined by the first tamp, the female channel and male member aligning the tamps longitudinally.

9. The method of claim 5 further comprising inserting a guide rod into the intramedullary canal and wherein impaction grafting the first canal portion comprises moving the first and second tamps axially together over the guide rod and wherein impaction grafting the second canal portion comprises leaving the first tamp stationary in the first canal portion and moving the second tamp axially relative to the stationary first tamp.

10. A method for impaction grafting an intramedullary canal of a bone comprising:
   providing a first tamp;
   tamping the intramedullary canal by reciprocally moving the first tamp axially within the intramedullary canal;
   discontinuing tamping with the first tamp and leaving the first tamp within the intramedullary canal;
   providing a second tamp;
   mounting the second tamp to the first tamp in axial sliding relationship;
   tamping the intramedullary canal by reciprocally moving the second tamp relative to the first tamp within the intramedullary canal; and
   locking the first and second tamps together in fixed axial relationship to prevent relative axial movement between the first tamp and the second tamp before said step of tamping the intramedullary canal by reciprocally moving the first tamp axially within the intramedullary canal, whereby said step of tamping the intramedullary canal by reciprocally moving said first tamp axially within the intramedullary canal, comprises tamping the intramedullary canal by reciprocally moving both the first tamp and the second tamp axially within the intramedullary canal, and wherein said step of mounting the second tamp to the first tamp in axial sliding relationship comprises the step of unlocking the second tamp from the first tamp.

11. The method of claim 10, wherein the first tamp has a shape mimicking a femoral hip stem component and the second tamp has a shape mimicking a femoral hip stem component, the shape of the first tamp and the shape of the second tamp cooperating to form a practically continuous tamping surface when the second tamp abuts the first tamp.

* * * * *